United States Patent [19]
Scheibengraber

[11] Patent Number: 5,095,386
[45] Date of Patent: Mar. 10, 1992

[54] OPTICAL SYSTEM FOR GENERATING LINES OF LIGHT USING CROSSED CYLINDRICAL LENSES

[75] Inventor: Karl J. Scheibengraber, Milwaukee, Wis.

[73] Assignee: Charles Lescrenier, Milwaukee, Wis.

[21] Appl. No.: 517,376

[22] Filed: May 1, 1990

[51] Int. Cl.⁵ .................. G02B 13/08; G02B 3/06
[52] U.S. Cl. .................................. 359/668; 359/710
[58] Field of Search ............... 350/420, 421, 432–435; 359/668, 710

[56] References Cited

U.S. PATENT DOCUMENTS

| | | | |
|---|---|---|---|
| 3,629,594 | 12/1971 | Sandberg | 250/221 |
| 3,861,807 | 1/1975 | Lescrenier | 356/152 |
| 4,025,200 | 5/1977 | Zeineh | 356/201 |
| 4,083,239 | 4/1978 | Malcolm et al. | 356/252 X |
| 4,192,578 | 3/1980 | Suzuki et al. | 350/320 |
| 4,203,652 | 5/1980 | Hanada | 250/433 X |
| 4,230,942 | 10/1980 | Stauffer | 350/167 |
| 4,253,735 | 3/1981 | Kawamura et al. | 350/409 |
| 4,284,994 | 8/1981 | Radl | 350/6.8 X |
| 4,318,594 | 3/1982 | Hanada | 350/433 |
| 4,372,640 | 2/1983 | LaCroix | 350/6.3 |
| 4,393,408 | 7/1983 | Beck et al. | 350/6.3 X |
| 4,415,239 | 11/1983 | Humphrey | 350/420 X |
| 4,429,946 | 2/1984 | Haines | 350/3.76 |
| 4,474,438 | 10/1984 | Rebholz et al. | 350/420 X |
| 4,521,087 | 6/1985 | Hayes et al. | 350/574 |
| 4,589,738 | 5/1986 | Ozaki | 350/443 |
| 4,620,768 | 11/1986 | Tatsuno et al. | 350/6.8 |
| 4,627,685 | 12/1986 | Sakuma | 350/6.8 |
| 4,636,080 | 1/1987 | Feldman | 356/401 |
| 4,643,516 | 2/1987 | Ogura | 350/6.8 |
| 4,693,567 | 9/1987 | Ozaki | 350/433 |
| 4,720,632 | 1/1988 | Kaneko | 250/235 |
| 4,733,944 | 3/1988 | Fahlen et al. | 350/167 |
| 4,820,911 | 4/1989 | Arackellian et al. | 350/6.8 X |

FOREIGN PATENT DOCUMENTS

57-204018  12/1982  Japan ...................... 350/420

OTHER PUBLICATIONS

Volosov et al.; "Effect of the Spatial Structure of a Lasar Beam on the Generation of the Second Harmonic in ADP and KDP Crystals"; *Optics & Spectroscopy*; vol. 21, No. 6; pp. 392–394.

Brochure published by Gammex, Inc. describing "THER-A-CROSS X Laser System" which generates lines of light for use in patient positioning, 1989.

*Primary Examiner*—Scott J. Sugarman
*Attorney, Agent, or Firm*—Lathrop & Clark

[57] ABSTRACT

An optical system for generating lines includes a source of a diverging light beam, a first cylindrical lens (104) which receives the light beam, and a second adjacent cylindrical lens (106) which is at an angle with respect to the first. The beam of light passes through the first and second cylindrical lenses (104, 106) to produce a planar beam of light (124) which becomes a line (122) when incident upon a surface (126). The cylindrical lenses (104, 106) are mounted so as to be rotatable both simultaneously and with respect to each other. The angle of the line generated by the lens configuration is a bisector of the obtuse angles formed by the principal axes of the cylindrical lenses (104, 106) except where the lenses are at right angles to one another. The rotation of both lenses simultaneously changes the angle of the line (128) while rotation of one lens with respect to the other adjusts the focus of the line. The system generates long, sharp lines of substantially even brightness along the length of the line while allowing control of the focus (zoom capability) and the length of the projected line, and enabling two short focal length lenses to perform like one long focal length lens. The system for generating lines may be used as part of a patient positioning system.

47 Claims, 4 Drawing Sheets

OPTICAL SYSTEM FOR GENERATING LINES OF LIGHT USING CROSSED CYLINDRICAL LENSES

FIELD OF THE INVENTION

This invention pertains generally to Optical alignment and metrological systems using optical systems to generate lines of light, and particularly to patient positioning systems designed for therapeutic and diagnostic medical equipment.

BACKGROUND OF THE INVENTION

For radiation therapy procedures using linear accelerators, simulators, cobalt 60 machines, or the like, precise patient positioning is critical if therapy is to be a benefit. Typically, a patient is placed on a patient positioning device, such as a cradle or bed and the portion of the patient to be treated is placed in a radiation beam for an exposure of predetermined duration. The irradiation of the patient destroys cellular tissue or inhibits its growth to achieve the desired therapeutic benefits. As can be readily appreciated, the radiation beam must be accurately positioned with respect to the portion of a patient being treated both to insure the maximum therapy and to prevent undesirable damage to healthy tissue. To achieve the accuracy necessary for such procedures, a laser system has been used to provide horizontal, transverse, and sagittal lines of laser light that identify the therapy axis and define the exact isocenter of the radiation equipment for patient positioning.

Such positioning has commonly been carried out by locating an anatomical landmark on the patient or painting a target on the patient's skin to be irradiated. A light pattern, for example, a cross-hair or an "X", is provided along the path of the radiation beam and the patient's couch is moved so that the target on the skin is aligned with the lighted pattern. The lighted pattern may then be removed, the area around the patient evacuated of personnel and the radiation beam established.

In the creation of a light pattern to position the patient, laser lines are generated by an apparatus typically comprising a laser, a beam expanding telescope, and a cylindrical lens, all of which are mounted within a wall hung cabinet. In such a design there are three axes that must be aligned: (1) the laser tube axis, (2) the telescope axis, and (3) the diverging lens or turret axis. The telescope portion of the laser line generator may comprise a pair of expensive spherical lenses. The lenses must be adjusted and arranged to produce laser lines of sufficient length, brightness, acuity, and depth of field. Because of the geometry of the lens configurations for laser line generators of the prior art, the telescope is typically buried deep in the cabinet, which is inconvenient for making necessary adjustments. For lens configurations of the prior art utilizing a beam splitter (for double-line or "cross" generators) and mirrors to direct the light beam emanating from the laser, additional adjustments must be made. The lens configurations for laser line generation in accordance with the prior art are therefore usually time-consuming to adjust and often require expensive optics.

SUMMARY OF THE INVENTION

In summary, the present invention comprises crossing a pair of cylindrical lenses in a light beam to jointly or severally control the focus and length of the image of the light source. The beam can be diverging or collimated light from a laser, an optical fiber transmitting light from a remote source, or other spot sources, or diverging light from a line source (e.g., an incandescent filament, a row of optical fibers, a row of LED's, etc.) Advantages of the invention include long focus performance from short-focus cylindrical lenses, longer lines than are obtainable with a single cylindrical lens, and zoom capability (i.e., the lenses can be crossed at different angles to get different focal lengths), and additional advantages as discussed further below.

In accordance with the present invention, an optical system for generating lines of light includes a light source such as a laser, a lens arrangement that preferably diverges the collimated beam from the laser, and a set of two plano-convex or convex-convex cylindrical lenses positioned to intercept the diverged laser beam. The plano-convex cylindrical lenses each have a planar surface and a convex surface through which the laser beam is directed and are preferably positioned closely adjacent to each other, typically with either the planar surfaces or the convex surfaces back-to-back. One or both of the lenses may be convex-convex, that is, a full cylinder. After traveling through the two cylindrical lenses, the diverging laser beam becomes effectively a thin plane of light. Upon striking a surface, the plane of light appears as a line.

The cylindrical lenses in a pair are preferably mounted so as to be rotatable simultaneously and also with respect to each other. The line generated by the lens configuration of the present invention is parallel with the long principal axis of one of the lenses if they are oriented at 90° with respect to each other. Otherwise, the line generated is a bisector of the obtuse angles formed by the principal axes (i.e. the non-power axes) of the two cylindrical lenses. The rotation of both cylindrical lenses of a set at the same time changes the angle of the laser line that is produced. By rotating one of the cylindrical lenses with respect to the other, the focus of the line can be adjusted. The present invention allows long patient alignment lines with sub-millimeter line widths to be generated. Asphericity produced by the crossed lenses can contribute to even brightness along the length of the line.

The two cylindrical lenses can effectively perform the function of the telescope used in the prior art to determine line width and to focus the line. The cylindrical lenses used in the present invention are relatively inexpensive compared to the achromatic optics used in the telescope of the prior art. Further, the present invention does not require precise alignment of as many lens axes and thus eliminates the alignment difficulties of the prior art. If the optical system of the present invention is used to direct one or more lines at a target, fine X-Y movement of the lines may be accomplished by X-Y translation of the two cylindrical lenses. While the adjustments to the laser line generator of the prior art may have been difficult due to the inaccessability of the telescope within the cabinet, the adjustments to the present optical system are simply performed by, for example, rotation or translation of lensholders conveniently located in the front or on top of the cabinet. The lensholders can allow both cylindrical lenses of a set to turn simultaneously or can allow one to be turned with respect to the other.

The lens configuration of the present invention is usable in many applications for projected lines of light which may be used for alignment, measuring, or the like. Long and thin lines can be produced from nonlaser sources such as light-emitting diodes or small filament incandescent bulbs. The present invention is particularly well suited to a patient positioning system in which a patient is aligned for therapeutic or diagnostic medical procedures.

Further objects, features and advantages of the invention will be apparent from the following detailed description taken in conjunction with the accompanying drawings.

DESCRIPTION OF THE PREFERRED EMBODIMENTS

Figure 1:
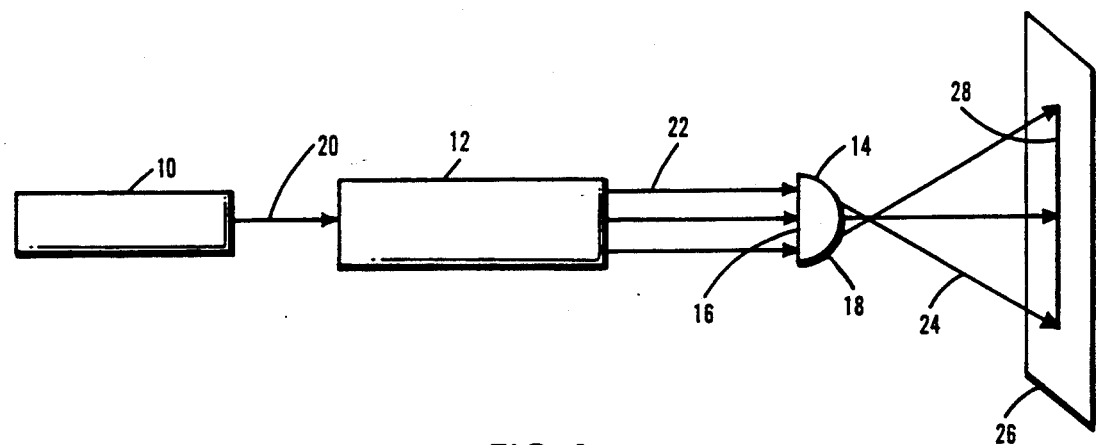
FIG. 1 is a schematic representation of a prior art optical system for generating a line of light.

With reference to the drawings, a typical prior art optical system for generating a line of light, such as for use in a patient positioning system, is shown schematically in FIG. 1. The optical system for line generation of the prior art comprises a laser 10, a telescope 12, and a plano-convex cylindrical lens 14 having a planar surface 16 and a convex surface 18. A narrow, substantially collimated beam of light 20 emanating from the laser 10 is directed into the eyepiece of the telescope 12. Traveling through the telescope 12, the beam of light 20 is diverged and re-collimated according to the properties of the telescope 12 to become a beam 22. The beam 22 is then incident upon the planar surface 16 of the cylindrical lens 14. The cylindrical lens 14 diverges the beam 22 into a plane of light 24. The plane of light 24 is directed in a plane radially outward from the convex surface 18 of the plano-convex cylindrical lens 14. Thus, in the orientation of the cylindrical lens 14 as depicted in FIG. 1, the plane of light 24 is parallel to the page on which FIG. 1 is drawn. When incident upon a surface 26 (shown rather close and oriented at an angle with respect to the page for illustrative purpose), the planar beam of light 24 becomes a line 28.

Figure 2:
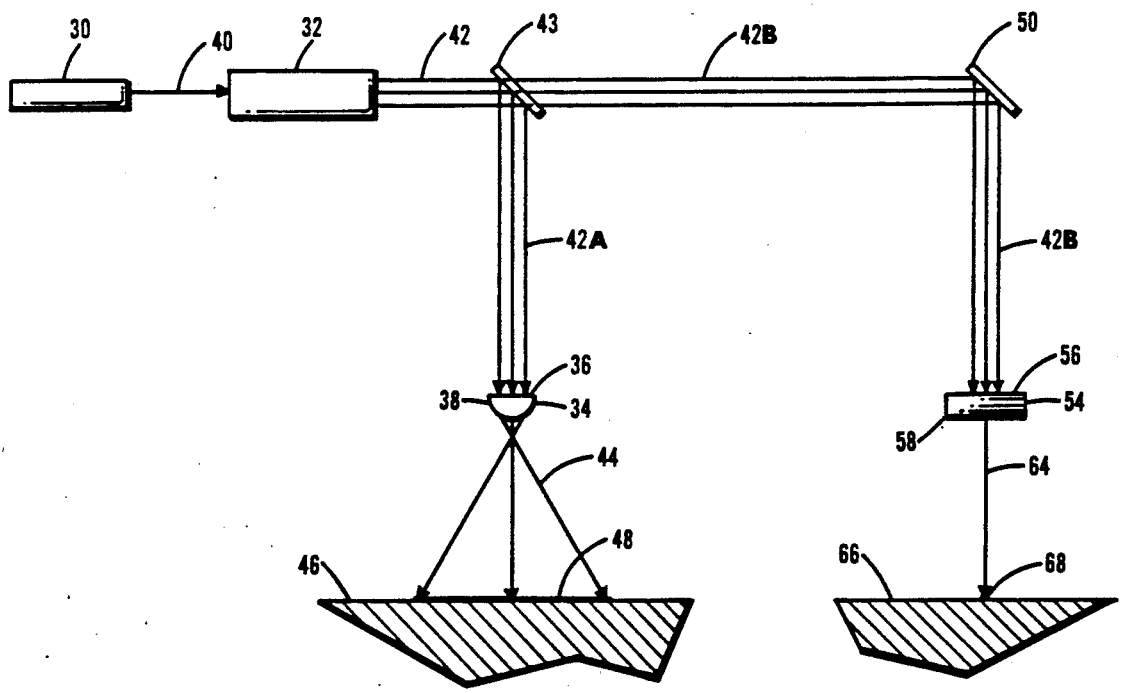
FIG. 2 is a schematic representation of an alternate prior art optical system for generating double lines of light.

FIG. 2 represents a second example of a prior art optical system for generating double lines of light. For this case, a laser 30, a telescope 32, a beam of light 40, and a beam of light 42 are respectively analogous to the laser 10, the telescope 12, the beam of light 20 and the beam of light 22 of FIG. 1. The beam of light 42 strikes a beam splitter 43 to create light beams 42A and 42B. The beam 42A is then incident upon a first cylindrical lens 34 having a planar surface 36 and a convex surface 38. The first cylindrical lens 34 diverges the beam 42A into a plane of light 44. The plane of light 44 is directed in a plane radially outward from the convex surface 38 of the plano-convex cylindrical lens 34. Thus, in the orientation of the cylindrical lens 34 as depicted in FIG. 2, the plane of light 44 is parallel to the page on which FIG. 2 is drawn. When incident upon a surface 46, the plane of light 44 becomes a line 48. The beam 42B strikes a mirror 50 and is then reflected to be incident upon a second plano-convex cylindrical lens 54 having a planar surface 56 and a convex surface 58. The second cylindrical lens 54 diverges the beam 42B into a plane of light 64. The planar beam of light 64 is directed in a plane radially outward from the convex surface 58 of the plano-convex cylindrical lens 54. Thus, in the orientation of the cylindrical lens 54 as depicted in FIG. 2, the plane of the beam of light 64 is perpendicular to the page on which FIG. 2 is drawn. When incident upon a surface 66 (which typically is the same as the surface 46), the plane of light 64 becomes a line 68. The line 48 is perpendicular to the line 68.

In the above described prior art optical systems for generating lines, the depth of field and the width of the lines 28, 48, and 68 are controlled by the properties of the telescopes 12 and 32. Because of the limited amount of space that is typically available to work with, the spherical lenses within the telescopes 12 and 32 are expensive, having a very short focal length and correction for spherical aberration. Further, the optical systems of the prior art have three axes that must be aligned to be colinear: the axis of the tube of the laser, the telescope axis and the axis of the mount in which each cylindrical lens is held.

Figure 3:
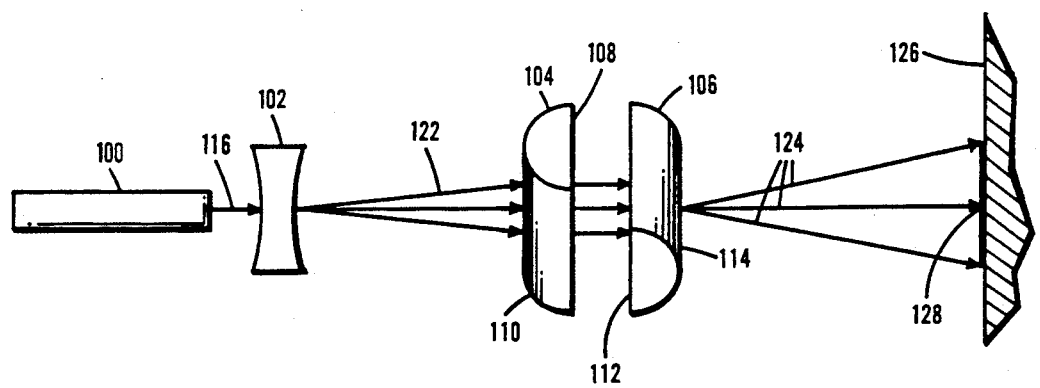
FIG. 3 is a schematic representation of an optical system for generating a line of light in accordance with the present invention.
Figures 5, 6:
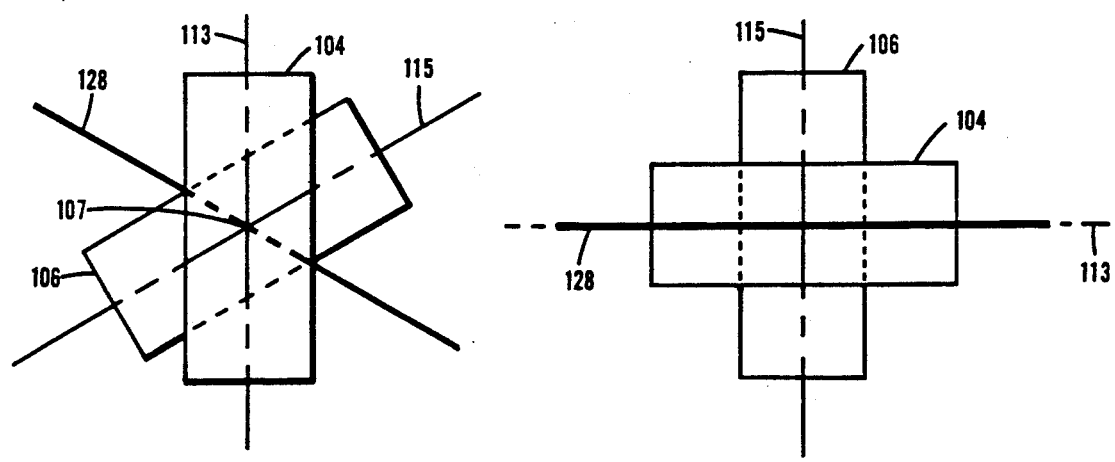
FIG. 5 is an illustrative view along the central axis of the crossed lenses of FIG. 3 illustrating the orientation of the generated line of light.
FIG. 6 is an illustrative view of the crossed lenses of FIG. 5 in a different angular orientation to one another.

FIG. 3 shows an optical system for generating a line of light in accordance with the present invention. The present invention comprises a laser 100, a spherical concave-concave diverging lens 102, a first plano-convex cylindrical lens 104 and a second plano-convex cylindrical lens 106 positioned closely adjacent the first lens. The laser used in the present invention is preferably a helium-neon laser, though other types, e.g. semiconductor lasers may also be used. Further, other high intensity light sources that produce an intense light beam may be substituted for the laser 100 and diverging lens 102 herein specified. The first plano-convex cylindrical lens 104 has a planar surface 108 and a convex surface 110. The second plano-convex cylindrical lens 106 has a planar surface 112 and a convex surface 114. FIG. 5 is a view of the lenses 104 and 106 looking directly along the central axis 107 of the lenses, with the lenses oriented at different angles than shown in FIG. 3. As an example of suitable optical elements, the lens 102 may be a −20 mm spherical lens to diverge the beam from the laser, the lens 104 may be a +20 mm cylindrical lens to further diverge the beam into an unfocused line, and the lens 106 may be a +75 mm cylindrical lens to do the final focusing.

As shown in FIG. 5, the planar surface 108 and the convex surface 110 of the first plano-convex lens 104 are directed along, that is, parallel to a non-power axis 113. The non-power axis 113 extends in the direction of the axis of the theoretical cylinder of which the convex surface 110 forms a section. There is no refraction in the non-power axis. The plano-convex cylindrical lens 106 has a corresponding non-power axis 115. The non-power axis 113 and the non-power axis 115 intersect at the central axis 107 when projected upon each other. The first cylindrical lens 104 and the second cylindrical lens 106 are preferably rotatable with respect to one another. Such rotation is generally about the axis 107 that extends through the centroid of the planar surfaces 108 and 112 and the convex surfaces 110 and 114.

A beam of light 116 emanating from the laser 100 is directed into the diverging lens 102, causing the beam 116 to diverge and become a beam 122. The beam 122 is then incident upon the convex surface 110 of the first cylindrical lens 104 and then exits the planar surface 108 of the first cylindrical lens 104. The beam 122 then enters the planar surface 112 of the second cylindrical lens 106 and exits the convex surface 114 thereof. The first and second cylindrical lenses 104 and 106 convert the beam 122 into a diverging planar beam of light 124. The plane of the beam of light 124 is oriented in a direction that represents the bisector of the obtuse angles between the non-power axes of the cylindrical lenses 104 and 106. When incident upon a wall or other surface 126, the planar beam of light 124 becomes a line 128, the orientation of which is best illustrated in FIG. 5. The optical system provides a line which has large depth of field, so that it will be sharply focused on walls at various distances from the lenses (e.g., 3 to 10 meters) and will be relatively long (several meters) and narrow (on the order of a millimeter).

FIG. 6 is a view of the lenses 104 and 106 similar to that of FIG. 5 but with the non-power axes 113 and 115 of the lenses oriented at right angles to one another. For this special case, the plane of light 124 emanating from the lens 106, and the line 128 formed on a wall, are parallel to one of the non-power axes, e.g., the axis 113 for the lens arrangement of FIG. 6. As the lenses 104 and 106 are rotated with respect to one another so that the angle between the non-power axes approaches 90°, the line 128 defocuses and can be re-focused by changing its distance to the source until it is parallel to one of the non-power axes.

The length of the line 128 on a surface at a certain distance from the lens set is determined by the focal length of one or both of the cylindrical lenses — generally, short focal lengths produce longer lines. The relative length of the line thus can be selected by proper selection of the focal length of the lenses.

The diverging lens 102 serves to diverge the tightly collimated beam 116 from the laser 100 into a beam which, when incident on the first lens 104, substantially fills the aperture of that lens. The distance between the light source (e.g., laser 100 and lens 102) and the first cylindrical lens 104 is determined by the angle between the lenses 104 and 106. As an alternative to the laser 100 and diverging lens 102, the light can be provided from an optical fiber (not shown) to the cylindrical lens set. It is also understood that light sources other than lasers can be used, although a laser may be desirable because it produces a very high intensity light beam which is monochromatic.

Figure 4:
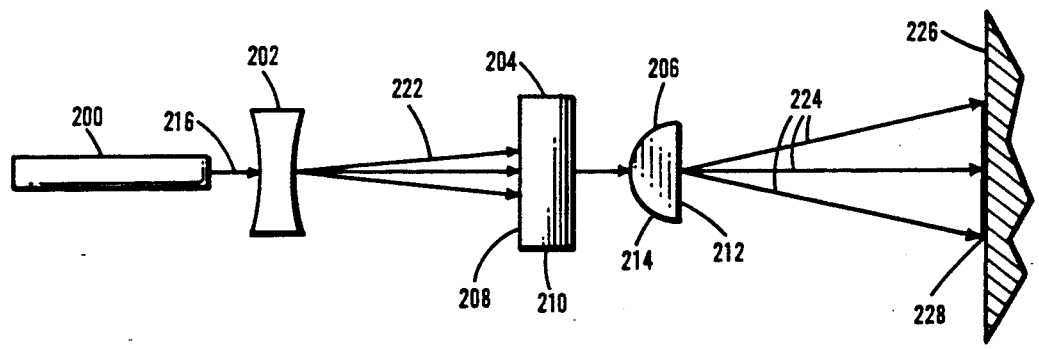
FIG. 4 is a schematic representation of an alternate optical system for generating a line of light in accordance with the present invention.

FIG. 4 is an an alternate optical system for generating a line of light in accordance with the present invention. The configuration of FIG. 4 comprises a laser 200, a diverging lens 202, a first plano-convex cylindrical lens 204 and a second plano-convex cylindrical lens 206. The first plano-convex cylindrical lens 204 has a planar surface 208 and a convex surface 210. The second plano-convex cylindrical lens 206 has a planar surface 212 and a convex surface 214. The first cylindrical lens 204 and the second cylindrical lens 206 are preferably but need not be rotatable with respect to one another. A beam of light 216 emanating from the laser 200 is directed into the diverging lens 202, causing the beam 216 to diverge and become a beam 222 which is then incident upon the planar surface 208 of the first cylindrical lens 204 and exits its convex surface 210. The beam 222 then enters through the convex surface 214 of the second cylindrical lens 206 and then exits from the planar surface 212 of the lens 206. The first and second cylindrical lenses 204 and 206 convert the beam 222 into a diverging planar beam of light 224. In the optical system of FIG. 4, the convex surfaces of the cylindrical lenses face each other, whereas in the system of FIG. 3, the planar surfaces face each other. Generally, the configuration of FIG. 3 is preferable, since a better defined line is formed when the convex surface faces the collimated beam, e.g., when the convex surface 114 is the surface from which the (one dimensionally) collimated plane of line 124 exits. It is noted that the lenses in a set may be oriented so that the planar and convex surfaces face in the same direction.

The plane of light 224 is oriented along the bisector of the obtuse angles between the non-power axes except when the axes are at right angles, in which case the plane of light 224 and the line 228 formed on a wall 226 lie parallel with one of the non-power axes.

Figure 7:
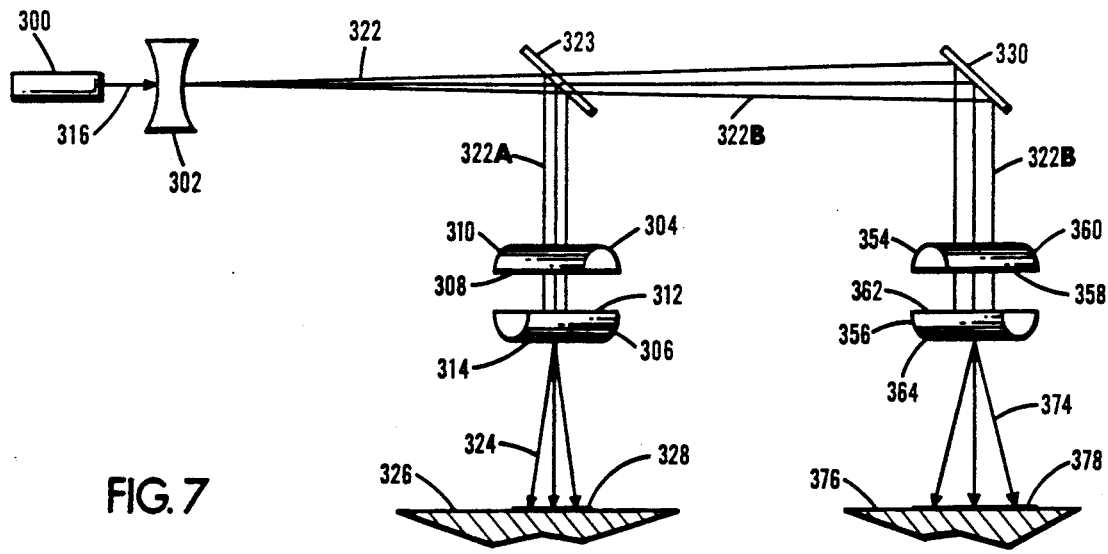
FIG. 7 is a schematic representation of an optical system for generating double lines of light in accordance with the present invention.

FIG. 7 shows an optical system for generating double lines of light in accordance with the present invention. For this system, a laser 300, a diverging lens 302, a beam of light 316, and a beam of light 322 are respectively analogous to the laser 100, the the diverging lens 102, the beam of light 116, and the beam of light 122 of FIG. 3. The optical system of FIG. 7 further comprises a beam splitter 323, a mirror 330, a first plano-convex cylindrical lens 304, a second plano-convex cylindrical lens 306, a third plano-convex cylindrical lens 354 and a fourth plano-convex cylindrical lens 356. The first plano-convex cylindrical lens has a planar surface 308 and a convex surface 310. The second plano-convex cylindrical lens has a planar surface 312 and a convex surface 314. The first cylindrical lens 304 and the second cylindrical lens 306 are rotatable with respect to one another. The third plano-convex cylindrical lens 354 has a planar surface 358 and a convex surface 360. The fourth plano-convex cylindrical lens 356 has a planar surface 362 and a convex surface 364. The third plano-convex cylindrical lens 354 and the fourth plano-convex cylindrical lens 356 are rotatable with respect to one another. The beam of light 316 emanating from the laser 300 is directed into the diverging lens 302, causing the beam 316 to diverge and become the beam 322. The beam 322 strikes the beam splitter 323 to create light beams 322A and 322B. The beam 322A is then incident upon the convex surface 310 of the first cylindrical lens 304 and then exits from its planar surface 308. The beam then enters the planar surface 312 of the second cylindrical lens 306 and exits from the convex surface 314. The first and second cylindrical lenses 304 and 306 convert the beam 322 into a diverging planar beam of light 324. The plane of the beam of light 324 is oriented in a direction that represents the bisector of the obtuse angles between the non-power axes of the cylindrical lenses 304 and 306. When incident upon a surface 326, the plane of light 324 becomes a line 328.

The beam 322B strikes the mirror 330 and is then reflected to be incident upon the convex surface 360 of the third cylindrical lens 354 and then exits from its planar surface 358. The beam 322B then enters the planar surface 362 of the fourth cylindrical lens 356 and exits from its convex surface 364. The third and fourth cylindrical lenses 354 and 356 convert the beam 322B into a diverging planar beam of light 374. The plane of the beam of light 374 is again oriented in a direction that represents the bisector of the obtuse angles between the non-power axes of the cylindrical lenses 304 and 306. When incident upon a surface 376, the plane of light 374 becomes a line 378. The line 378 can be oriented by rotating the lenses 354 and 356 together. In typical applications, the line 378 will be perpendicular to the line 328 and the two together form a cross.

In accordance with the present invention, it is preferred that the two cylindrical lenses in each pair be rotatable with respect to one another. All of the aforementioned pairs of cylindrical lenses preferably are also rotatable as a set, so that both cylindrical lenses of a pair may be rotated together. As noted above, each of the lines 128, 228, 328, and 378 are bisectors of the obtuse angles formed by the principal axes (i.e. the non-power axes) of the cylindrical lenses of a set, except in the special case where the lenses are at right angles to one another. The combined refraction may be aspheric in cross-section and the relatively short focal length of one of the cylindrical lenses in a set can result in a much longer line than a line generated by a single cylindrical lens as in the prior art. The aspheric refraction may serve to even out the brightness along the length of the line. The focus of the lines 128, 228, 338 and 378 at a given distance, or the focus of the lines at different distances, is adjustable by rotation of one of the lenses of a set with respect to the other. The resultant lines 128, 228, 328, and 378 can thus be focused to be extremely sharp and may be sub-millimeter in thickness. The gap distance between the cylindrical lenses of a set is not critical, although it is preferred that the lenses be close enough together that all of the light emanating from the first lens is captured by the second.

Turning both cylindrical lenses of a set at the same time changes the angle of the projected line. In prior art line generators, adjustments of the focus were made by adjusting the telescope. Where such line generators are attached to a wall, for example, adjustments may be difficult because the telescope may not be easily reached. In the optical systems for generating lines of light of the present invention, adjustments to the focus may be more easily made inasmuch as the cylindrical lenses generally would be located toward the front or top of the line generator apparatus. The lenses and other components of the optical system for generating lines of light may be mounted within a turret, which is, in turn, mounted in a wall-hung cabinet. In the present invention, adjustments to the focus may be made by rotating one or both of two lensholders in which the cylindrical lenses are mounted. Either lensholder may be turned to rotate one of the cylindrical lenses with respect to the other. Both of the lensholders may be turned simultaneously to rotate the lenses as a set and change the angle of the projected line of light.

Figure 8:
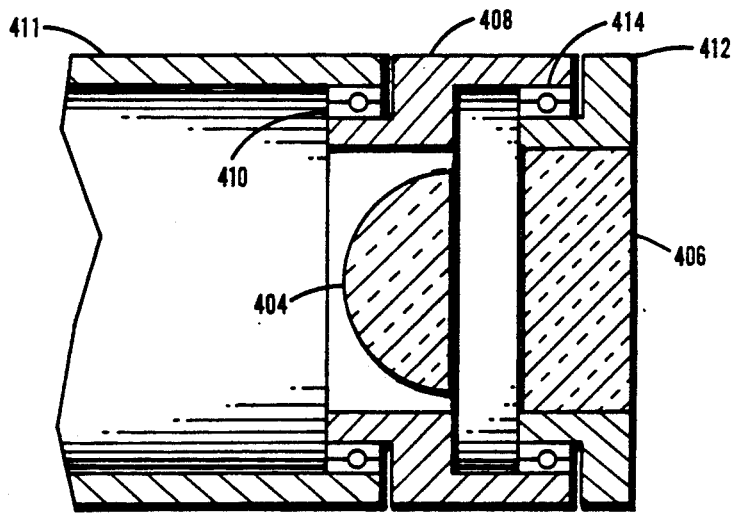
FIG. 8 is a cross-sectional view through a portion of the lensholder of the optical system of the invention, showing an exemplary structure for mounting the crossed cylindrical lenses for rotation of the lenses both as a set and with respect to one another.

FIG. 8 is a section view through a portion of a compound lensholder, showing an exemplary arrangement for rotation of the cylindrical lenses both as a set and with respect to one another. The cylindrical lenses of the set are designated at 404 and 406, although it is understood that they are meant to be representative of all of the sets of lenses depicted in FIGS. 3, 4, and 5. The cylindrical lens 404 is mounted within a lensholder sleeve 408 which is mounted for rotation with respect to the barrel 411 (partially shown in FIG. 8) on a bearing 410. Because the sleeve 408 will not be rotated frequently, the bearing 410 may be omitted and the sleeve 408 can be directly mounted to the barrel 411 in sliding rotational engagement. The cylindrical lens 406 is mounted within a lensholder sleeve 412 which is mounted for rotation with respect to the lensholder sleeve 408 on a bearing 414 (which again may be omitted). Although not shown in FIG. 8, the other elements of the system include a diverging lens and a laser as previously described. The cylindrical lenses 404 and 406 may be rotated together as a set by turning the lensholder 408 with respect to the barrel 411, or they may be rotated with respect to each other, e.g., the cylindrical lens 406 may be rotated by turning the lensholder 412 while the lensholder 408 is held stationary. Other configurations which obtain the necessary rotation of the cylindrical lenses may also be utilized.

It is also to be understood that further embodiments of the invention may be obtained having more than two sets of cylindrical lenses, using additional beam splitters, in which the cylindrical lenses may be positioned with either their planar surfaces or convex surfaces positioned back-to-back or in the same direction. The use of multiple beam splitters is therefore to be understood as within the scope of the present invention.

Figure 9:
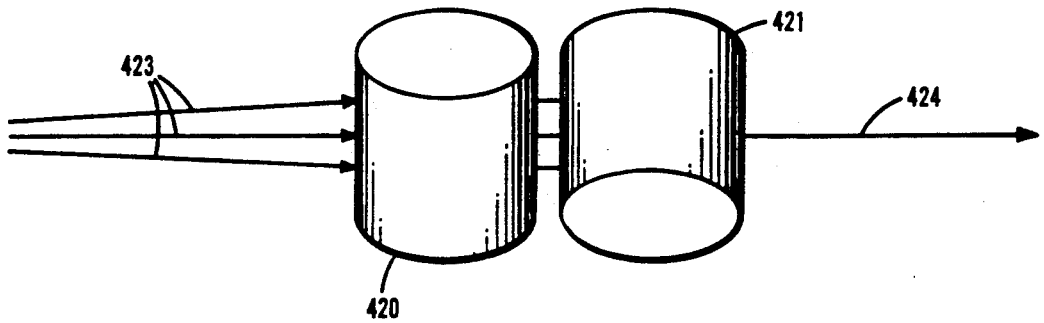
FIG. 9 is an illustrative view of crossed convex-convex (fully cylindrical) lenses in accordance with the invention.

As illustrated in FIG. 9, fully cylindrical (convex-convex) lenses 420 and 421 may be utilized in accordance with the invention, substituting for any of the sets of lenses in the configurations of FIGS. 3, 4, and 7. An incoming (diverging) beam enters the lens 420 and exits the lens 421 as a plane of light 424 which will be seen as a line when incident on a wall. The angle of the plane of light 424 is again the bisector of the obtuse angles between the principal axis of the lenses 420 and 421 except where the lenses are at right angles to one another. In the latter case, the plane of light is coincident with one of the principal axes. Generally, fully convex-convex lenses would be used for close focal distances. It is also understood that one of the cylindrical lenses in a pair may be convex-convex and the other may be planar-convex, it being understood that both types of lenses are referred to herein as cylindrical lenses. It may also be noted that in some limited applications it may be possible to substitute a cylindrical reflecting element for a cylindrical lens.

Figure 10:
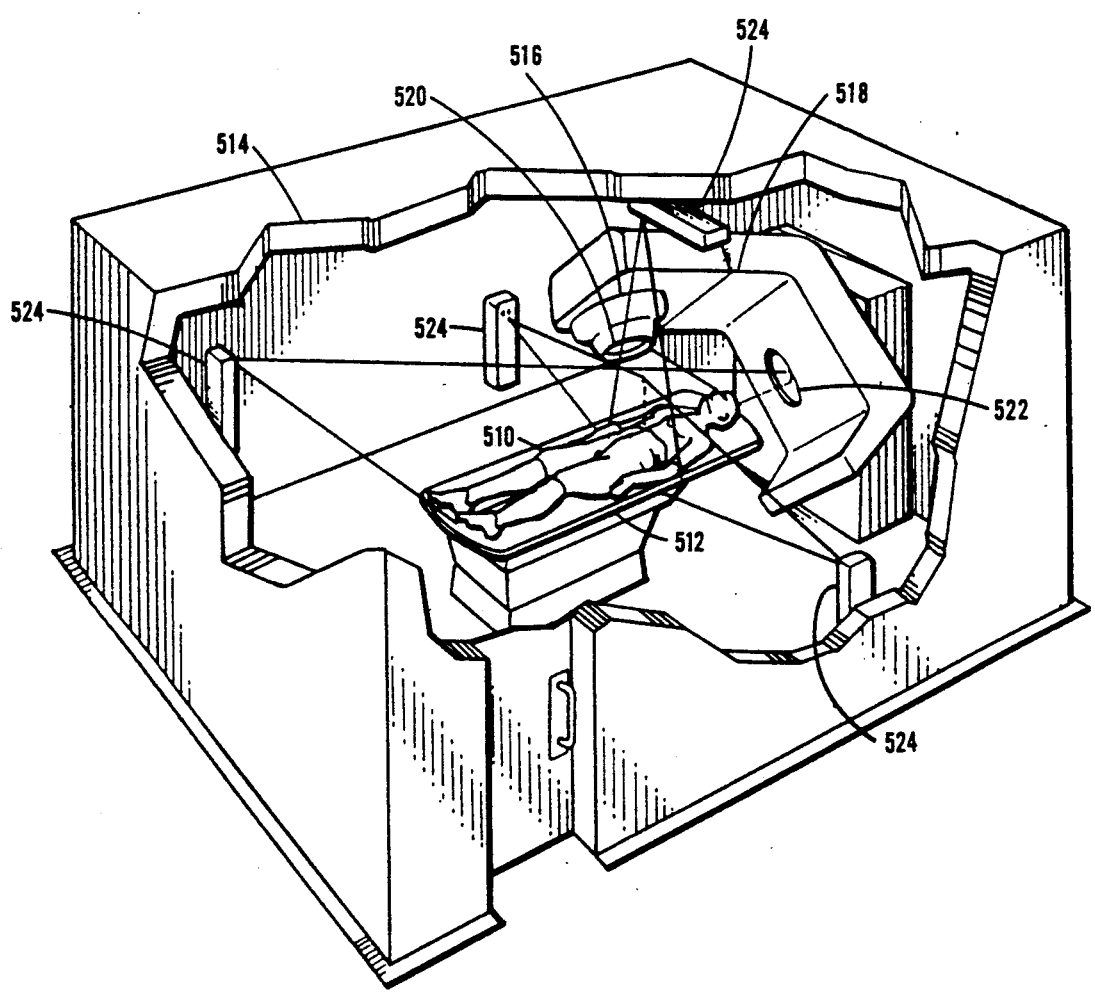
FIG. 10 is an illustrative view showing the optical system for generating lines of light adapted for use in a patient positioning system, the room being partially cut away.

FIG. 10 depicts an exemplary application of the present system for line generation as a means for positioning a patient with respect to a radiation beam. A patient 510 is positioned upon a patient positioning device, such as a cradle 512 within a shielded room 514. A radiation source 516 includes an arm 518 that supports a head 520 for emitting radiation. The arm 518 is arcuately moveable about a pivot axis 522 to apply the radiation beam with a desired degree of obliqueness. The head 520 may also be rotatable, to assist in directing the radiation beam.

The patient 510 is positioned on the cradle 512 in the intended path of the radiation. The cradle 512 can be raised or lowered within the room 514. The room 514 has a plurality of wall-mounted alignment line projectors 524 that produce cross-hair line patterns upon the patient 510. The line projectors 524 each contain an optical system in accordance with the present invention as has been previously described. The line projectors 524 provide horizontal, transverse, and sagittal lines of light that identify the therapy axis and that define the exact isocenter of the beam produced by the radiation equipment. Adjustments to the focus and angle of the lines may be effected by rotation of the cylindrical lenses in each line generator 524; rotation of the cylindrical lenses with respect to each other changes the focus of the line while simultaneous rotation of the cylindrical lenses changes the angle of the line. As previously described, such adjustments may be accomplished by having lensholders in which a set of cylindrical lenses are mounted so as to be accessible to a technician.

Though the lens configuration of the present invention is well-suited for use in a patient positioning system, it is to be understood that the present invention may be used in any application in which lines of light are to be generated.

It is understood that the invention is not confined to the particular construction and arrangement of parts herein illustrated and described, but embraces such modified forms thereof as come within the scope of the following claims.

What is claimed is:

1. An optical system for generating a line of light on a surface comprising:
    (a) a light source that produces an intense diverging or collimated light beam;
    (b) a first cylindrical lens positioned to receive the light beam and having a convex surface directed along a first lens non-power axis; and
    (c) a second cylindrical lens positioned adjacent to the first lens to receive the light beam exiting the first cylindrical lens and having a convex surface directed along a second lens non-power axis, the second cylindrical lens being positioned such that the light beam exiting the first cylindrical lens enters through a surface of the second cylindrical lens and exits through another surface of the second cylindrical lens as a planar beam of light which forms a line of light when incident upon a surface, the first and second cylindrical lenses being arranged such that the first and second non-power axes intersect, and wherein the cylindrical lenses are plano-convex lenses and the first cylindrical lens is positioned such that the light beam enters through its planar surface and exits through its convex surface and the second cylindrical lens is positioned such that the light beam enters through its convex surface and exits through its planar surface.

2. An optical system for generating a line of light on a surface comprising:
    (a) a light source that produces an intense diverging or collimated light beam;
    (b) a first cylindrical lens positioned to receive the light beam and having a convex surface directed along a first lens non-power axis; and
    (c) a second cylindrical lens positioned adjacent to the first lens to receive the light beam exiting the first cylindrical lens and having a convex surface directed along a second lens non-power axis, the second cylindrical lens being positioned such that the light beam exiting the first cylindrical lens enters through a surface of the second cylindrical lens and exits through another surface of the second cylindrical lens as a planar beam of light which forms a line of light when incident upon a surface, the first and second cylindrical lenses being arranged such that the first and second non-power axes intersect wherein the light source comprises a laser providing a light beam and a diverging lens positioned in the light beam between the laser and the first cylindrical lens.

3. The optical system of claim 2 wherein the non-power axes of the cylindrical lenses are oriented at right angles to one another.

4. An optical system for generating a line of light on a surface comprising:
    (a) a light source that produces an intense diverging or collimated light beam;
    (b) a first cylindrical lens positioned to receive the light beam and having a convex surface directed along a first lens non-power axis;
    (c) a second cylindrical lens positioned adjacent to the first lens to receive the light beam exiting the first cylindrical lens and having a convex surface directed along a second lens non-power axis, the second cylindrical lens being positioned such that the light beam exiting the first cylindrical lens enters through a surface of the second cylindrical lens and exits through another surface of the second cylindrical lens as a planar beam of light which forms a line of light when incident upon a surface, the first and second cylindrical lenses being arranged such that the first and second non-power axes intersect;
    (d) a beam splitter positioned in the light beam between the light source and the first cylindrical lens, the beam splitter dividing the light beam into two parts, the first part being directed to the first set of cylindrical lenses; and
    (e) a second set of adjacent cylindrical lenses, the second part of the light beam from the beam splitter being directed to the second set of cylindrical lenses.

5. The optical system of claim 4 wherein the light source comprises a laser providing a light beam and a diverging lens positioned in the light beam between the laser and the beam splitter.

6. The optical system of claim 5 wherein the laser is a helium-neon laser.

7. The optical system of claim 4 wherein the non-power axes of the cylindrical lenses are oriented at right angles to one another.

8. An optical system for generating a line of light on a surface comprising:
    (a) a light source that produces an intense diverging or collimated light beam;
    (b) a first cylindrical lens positioned to receive the light beam and having a convex surface directed along a first lens non-power axis;
    (c) a second cylindrical lens positioned adjacent to the first lens to receive the light beam exiting the first cylindrical lens and having a convex surface directed along a second lens non-power axis, the second cylindrical lens being positioned such that the light beam exiting the first cylindrical lens enters through a surface of the second cylindrical lens and exits through another surface of the second cylindrical lens as a planar beam of light which forms a line of lights when incident upon a surface, the first and second cylindrical lenses being arranged such that the first and second non-power axis intersect; and (d) means for rotating the first and second lenses with respect to one another to focus the line of light that is incident upon a surface.

9. The optical system of claim 8 wherein the non-power axes of the cylindrical lenses are oriented at right angles to one another.

10. An optical system for generating a line of light on a surface comprising:

(a) a light source that produces an intense diverging or collimated light beam;

(b) a first cylindrical lens positioned to receive the light beam and having a convex surface directed along a first lens non-power axis;

(c) a second cylindrical lens positioned adjacent to the first lens to receive the light beam exiting the first cylindrical lens and having a convex surface directed along a second lens non-power axes, the second cylindrical lens being positioned such that the light beam exiting the first cylindrical lens enters through a surface of the second cylindrical lens and exits through another surface of the second cylindrical lens as a planar beam of light which forms a line of light when incident upon a surface, the first and second cylindrical lenses being arranged such that the first and second non-power axes intersect; and (d) means for rotating the first and second lenses together as a set to adjust the angle of the line of light that is incident upon a surface.

11. An optical system for generating a line of light on a surface comprising:

(a) a light source that produces an intense diverging or collimated light beam;

(b) a first cylindrical lens positioned to receive the light beam and having a convex surface directed along a first lens non-power axis;

(c) a second cylindrical lens positioned adjacent to the first lens to receive the light beam exiting the first cylindrical lens and having a convex surface directed along a second lens, the second cylindrical lens being positioned such that the light beam exiting the first cylindrical lens enters a surface of the second cylindrical lens and exits through another surface of the second cylindrical lens as a planar beam of light which forms a line when incident upon a surface; and (d) means for rotating the first and second cylindrical lenses with respect to one another to change the angle between the first and second non-power axes to allow focusing of the line that is incident upon the surface.

12. The optical system of claim 11 wherein the first and second cylindrical lenses are plano-convex lenses and the first cylindrical lens is positioned such that the light beam enters through its convex surface and exits through its planar surface and wherein the second cylindrical lens is positioned such that the light beam enters through its planar surface and exits through its convex surface.

13. The optical system of claim 11 wherein the first and second cylindrical lenses are plano-convex lenses and the first cylindrical lens is positioned such that the light beam enters through its planar surface and exits through its convex surface and wherein the second cylindrical lens is positioned such that the light beam enters through its convex surface and exits through its planar surface.

14. The optical system of claim 11 wherein the light source comprises a laser providing a light beam and a diverging lens positioned in the light beam between the laser and the first cylindrical lens.

15. The optical system of claim 11 further including a beam splitter positioned in the light beam between the light source and the first cylindrical lens, the beam splitter dividing the light beam into two parts, the first part being directed to the first set of cylindrical lenses, and further including a second set of adjacent cylindrical lenses, the second part of the light beam from the beam splitter being directed to the second set of cylindrical lenses.

16. The optical system of claim 15 wherein the light source comprises a laser providing a light beam and a diverging lens positioned in the light beam between the laser and the beam splitter.

17. The optical system of claim 11 further including means for rotating the first and second cylindrical lenses together as a set to adjust the angle of the line.

18. The optical system of claim 16 wherein the laser is a helium-neon laser.

19. An optical system for generating a line of light on a surface comprising:

(a) a light source that produces an intense diverging or collimated light beam;

(b) a first cylindrical lens positioned to receive the light beam and having a convex surface directed along a first lens non-power axis;

(c) a second cylindrical lens positioned adjacent the first lens to receive the light beam exiting the first cylindrical lens and having a convex surface directed along a second lens non-power axis, the second cylindrical lens being positioned such that the light beam exiting the first cylindrical lens enters through a surface of the second cylindrical lens and exits through another surface of the second cylindrical lens as a planar beam of light which forms a line of light when incident upon a surface, the first and second cylindrical lenses being arranged such that the first and second non-power axes intersect; and (d) means for rotating the first and second cylindrical lenses together as a set to change the angle of the line that is incident upon the surface.

20. The optical system of claim 19 wherein the first and second cylindrical lenses are plano-convex lenses and the first cylindrical lens is positioned such that the light beam enters through its convex surface and exits through its planar surface and wherein the second cylindrical lens is positioned such that the light beam enters through its planar surface and exits through its convex surface.

21. The optical system of claim 19 wherein the first and second lenses are plano-convex lenses and the first cylindrical lens is positioned such that the light beam enters through its planar surface and exits through its convex surface and wherein the second cylindrical lens is positioned such that the light beam enters through its convex surface and exits through its planar surface.

22. The optical system of claim 19 wherein the light source comprises a laser providing a light beam and a diverging lens positioned in the light beam between the laser and the first cylindrical lens.

23. The optical system of claim 19 further including a beam splitter positioned in the light beam between the light source and the first cylindrical lens, the beam splitter dividing the light beam into two parts, the first part being directed to the first set of cylindrical lenses, and further including a second set of adjacent cylindrical lenses, the second part of the light beam from the beam splitter being directed to the second set of cylindrical lenses.

24. The optical system of claim 23 wherein the light source comprises a laser providing a light beam and a diverging lens positioned in the light beam between the laser and the beam splitter.

25. The optical system of claim 24 wherein the laser is a helium-neon laser.

26. The optical system of claim 19 wherein the non-power axes of the cylindrical lenses are oriented at right angles to one another.

27. A patient positioning system comprising:
(a) a light source that produces an intense diverging or collimated light beam;
(b) a first cylindrical lens positioned to receive the light beam and having a convex surface directed along a first lens non-power axis;
(c) a second cylindrical lens positioned adjacent to the first lens to receive the light beam exiting the first cylindrical lens and having a convex surface directed along a second lens non-power axis, the second cylindrical lens being positioned such that the light beam exiting the first cylindrical lens enters through a surface of the second cylindrical lens and exits through another surface of the second cylindrical lens as a planar beam of light which forms a line of light when incident upon a surface, the first and second cylindrical lenses being arranged such that the first and second axes intersect when projected upon each other; and
a patient positioning device upon which a patient may be placed for a medical procedure, the line of light being projected upon the patient to establish the location of the procedure to be administered.

28. The patient positioning system of claim 27 wherein the first and second cylindrical lenses are plano-convex lenses and the first cylindrical lens is positioned such that the light beam enters through its convex surface and exits through its planar surface and wherein the second cylindrical lens is positioned such that the light beam enters through its planar surface and exits through its convex surface.

29. The patient positioning system of claim 27 wherein the cylindrical lenses are plano-convex lenses and the first cylindrical lens is positioned such that the light beam enters through its planar surface and exits through its convex surface and wherein the second cylindrical lens is positioned so that the light beam enters through its convex surface and exits through its planar surface.

30. The patient positioning system of claim 27 wherein the light source comprises a laser providing a beam of light and a diverging lens positioned in the light beam between the laser and the first cylindrical lens.

31. The patient positioning system of claim 27 further including a beam splitter positioned in the light beam between the light source and the first cylindrical lens, the beam splitter dividing the light beam into two parts, the first part being directed to the first set of cylindrical lenses, and further including a second set of adjacent cylindrical lenses, the second part of the light beam from the beam splitter being directed to the second set of cylindrical lenses.

32. The patient positioning system of claim 31 wherein the light source comprises a laser providing a light beam and a diverging lens positioned in the light beam between the laser and the beam splitter.

33. The patient positioning system of claim 32 wherein the laser is a helium-neon laser.

34. The patient positioning system of claim 27 wherein the non-power axes of the cylindrical lenses are oriented at right angles to one another.

35. A method of generating a line of light on a surface comprising the steps of:
(a) directing an intense diverging or collimated light beam into a first cylindrical lens having a convex surface directed along a first lens non-power axis;
(b) directing the light exiting the first cylindrical lens into a second cylindrical lens having a convex surface directed along a second lens non-power axis to form a planar beam of light exiting the second cylindrical lens which forms a line of light when incident upon a surface; and
(c) rotating the first and second cylindrical lenses with respect to one another to focus the line of light.

36. The method of claim 35 wherein the first and second cylindrical lenses are plano-convex lenses and the light beam is directed to enter through the convex surface of the first cylindrical lens and exit through its planar surface and wherein the light exiting the first cylindrical lens is directed to enter through the planar surface of the second cylindrical lens and exit through its convex surface.

37. The method of claim 35 wherein the first and second cylindrical lenses are plano-convex lenses and the light beam is directed to enter through the planar surface of the first cylindrical lens and exit through its convex surface and wherein the light exiting the first cylindrical lens is directed to enter through the convex surface of the second cylindrical lens and exit through its planar surface.

38. The method of claim 35 wherein the step of directing an intense light beam further comprises the step of directing a narrow, substantially collimated light beam into a diverging lens prior to directing the light beam into the first cylindrical lens.

39. The method of claim 38 wherein the light beam is produced by a laser.

40. The method of claim 39 wherein the laser is a helium-neon laser.

41. The method of claim 35 further comprising the step of rotating the first and second cylindrical lenses together as a set to adjust the angle of the line of light.

42. A method of generating a line of light on a surface comprising the steps of:
(a) directing an intense diverging or collimated light beam into a first cylindrical lens having a convex surface directed along a first lens non-power axis;
(b) directing the light exiting the first cylindrical lens into a second cylindrical lens having a convex surface directed along a second lens non-power axis to form a planar beam of light exiting the second cylindrical lens which forms a line of light when incident upon a surface, the first and second cylindrical lenses being arranged such that the first and second non-power axes intersect; and (c) rotating the first and second cylindrical lenses together to change the angle of the line of light.

43. The method of claim 42 wherein the first and second cylindrical lenses are plano-convex lenses and the light beam is directed to enter through the convex surface of the first cylindrical lens and exit through its planar surface and wherein the light exiting the first cylindrical lens is directed to enter through the planar surface of the second cylindrical lens and exit through its convex surface.

44. The method of claim 42 wherein the first and second cylindrical lenses are plano-convex lenses and the light beam is directed to enter through the planar surface of the first cylindrical lens and exit through its convex surface and wherein the light exiting the first cylindrical lens is directed to enter through the convex surface of the second cylindrical lens and exit through its planar surface.

45. The method of claim 44 wherein the step of directing an intense light beam further comprises the step of directing a narrow, substantially collimated light beam into a diverging lens prior to directing the light beam into the first cylindrical lens.

46. The method of claim 45 wherein the light beam is produced by a laser.

47. The method of claim 46 wherein the laser is a helium-neon laser.

* * * * *

UNITED STATES PATENT AND TRADEMARK OFFICE
CERTIFICATE OF CORRECTION

PATENT NO. : 5,095,386

DATED : March 10, 1992

INVENTOR(S) : Scheibengraber

It is certified that error appears in the above-identified patent and that said Letters Patent is hereby corrected as shown below:

Column 11, line 7, "axis" should be -- axes --.

Column 11, line 24, "axes" should be -- axis--.

Column 13, line 40, insert -- (d) -- before "a patient positioning".

Signed and Sealed this

Fifteenth Day of June, 1993

Attest:

MICHAEL K. KIRK

Attesting Officer

Acting Commissioner of Patents and Trademarks